(12) United States Patent
Jeong et al.

(10) Patent No.: US 6,593,760 B2
(45) Date of Patent: Jul. 15, 2003

(54) APPARATUS FOR MEASURING THERMAL PROPERTIES AND MAKING THERMOMECHANICAL MODIFICATION ON SAMPLE SURFACE WITH PELTIER TIP

(75) Inventors: Yoon-Hee Jeong, Kyungsangbuk-do (KR); Dae-Hwa Jung, Kyungsanbuk-do (KR); Il-Kwon Moon, Daejeon (KR)

(73) Assignee: Pohang University of Science and Technology Foundation, Kyungsangbuk-Do (KR)

( * ) Notice: Subject to any disclaimer, the term of this patent is extended or adjusted under 35 U.S.C. 154(b) by 0 days.

(21) Appl. No.: 09/851,319

(22) Filed: May 9, 2001

(65) Prior Publication Data

US 2001/0048315 A1 Dec. 6, 2001

(30) Foreign Application Priority Data

May 10, 2000 (KR) ......................................... 2000-25038

(51) Int. Cl.$^7$ .............................................. G01R 17/02
(52) U.S. Cl. ......................................... 324/725; 374/43
(58) Field of Search .............................. 324/158.1, 765, 324/758.1, 760, 724, 725; 374/173, 179, 180, 181; 165/26–28

(56) References Cited

U.S. PATENT DOCUMENTS

| | | | | | |
|---|---|---|---|---|---|
| 3,534,809 A | * | 10/1970 | Jean | .............................. | 165/26 |
| 3,858,106 A | * | 12/1974 | Launius | ........................ | 165/27 |
| 5,222,396 A | * | 6/1993 | Takata et al. | .................. | 73/618 |
| 5,431,055 A | * | 7/1995 | Takata et al. | .................. | 73/618 |
| 5,441,343 A | * | 8/1995 | Pylkki et al. | ................ | 374/137 |
| 5,653,539 A | * | 8/1997 | Rosengaus | ................... | 374/159 |
| 5,865,978 A | * | 2/1999 | Cohen | ......................... | 205/118 |

* cited by examiner

*Primary Examiner*—Kamand Cuneo
*Assistant Examiner*—Jimmy Nguyen
(74) *Attorney, Agent, or Firm*—Leydig, Voit & Mayer, Ltd.

(57) ABSTRACT

An apparatus for measuring thermal properties and making thermomechanical modifications on a material surface using a junction of different metallic wires. The junction of different metallic wires, defined as a Peltier tip, is distinguished from a conventional thermocouple by the fact that it works as a point heat source and as a point temperature sensor simultaneously when an electric current flows into the tip. This novel functionality of the Peltier tip offers a way to thermally characterize a material surface with submicron-scale spatial resolution and high sensitivity, while providing high spatial resolution and speed for thermal modifications since both heating and cooling are possible at the Peltier tip.

4 Claims, 1 Drawing Sheet

APPARATUS FOR MEASURING THERMAL PROPERTIES AND MAKING THERMOMECHANICAL MODIFICATION ON SAMPLE SURFACE WITH PELTIER TIP

BACKGROUND OF THE INVENTION

1. Field of the Invention

The present invention relates to an apparatus for measuring the thermal properties of and making thermomechanical modifications an the surface of a particular material using a Peltier tip, which works as a heat source and as a temperature sensor simultaneously.

2. Description of the Related Art

In a semiconductor integrated circuit, heat generated per unit area increases as the integration density increases. To prevent occurrences of a short or a malfunction due to high temperature in an integrated circuit, the measurements of thermal properties of a semiconductor device are essential. The investigations of homogeneity of composite materials and the grain size of each individual material are important in the fields of medical science, material science, and chemical engineering, and so on. Also, in studying thin films or multilayer films, the precise measurements of thermal properties such as thermal conductivity and specific heat, which are fundamental physical quantities involving transport phenomena and internal degrees of freedom of a system, are required. Furthermore, the development of high density recording media is actively in progress through thermomechanical modifications of polymers and glassy films using a scanning thermal microscope.

As described above, the characterizations of thermal properties in the fields of semiconductors composites, and thin films are very important for engineering and scientific purposes. However, in an actual measurement, it is difficult to conduct quantitative analysis since the mass of a material is extremely small and the measurement apparatus has low spatial resolution.

Conventionally, a method of measuring thermal properties on a material surface includes the use of a Peltier tip made of a thin resistive wire as a heat source by applying a current to the tip, while measuring temperature through the change in resistance, thereby grasping thermal properties qualitatively. However, this method suffers from sensitivity limitations since the exchange of heat, generated over the entire tip by Joule heating, occurs only at a point that is in contact with a material. In addition, if the conventional method is applied to make thermomechanical modifications, there are limitations in spatial resolution and speed, since only heating is possible at the tip.

SUMMARY OF THE INVENTION

To solve the above problems, it is an object of the present invention to provide an apparatus for measuring thermal properties of and making thermomechanical modifications on a material surface using a Peltier tip. The Peltier tip is defined as a junction of different metallic wires, which is distinguished from a conventional thermocouple by the fact that it works as a point heat source and a point temperature sensor simultaneously when an electric current flows into the tip. This novel functionality of the Peltier tip offers the way to the thermal characterizations of a material surface with submicron-scale spatial resolution, and high sensitivity, while providing high spatial resolution and speed for thermal modifications since both heating and cooling are possible at the Peltier tip. The apparatus includes: a signal generator that drives an electric current into the Peltier tip; an ammeter connected to the signal generator for measuring current; a bridge circuit consisting of junctions of metallic wires, which is connected to the ammeter, wherein one junction of the metallic wires is made in the form of the Peltier tip; and a lock-in amplifier connected to both symmetrical terminals of the bridge circuit for amplifying and detecting voltages due to temperature oscillation detected by the Peltier tip.

BRIEF DESCRIPTION OF THE DRAWINGS

The above object and advantages of the present invention will become more apparent by describing in detail preferred embodiments thereof with reference to the attached drawings in which.

DETAILED DESCRIPTION OF THE INVENTION

Figure 1:
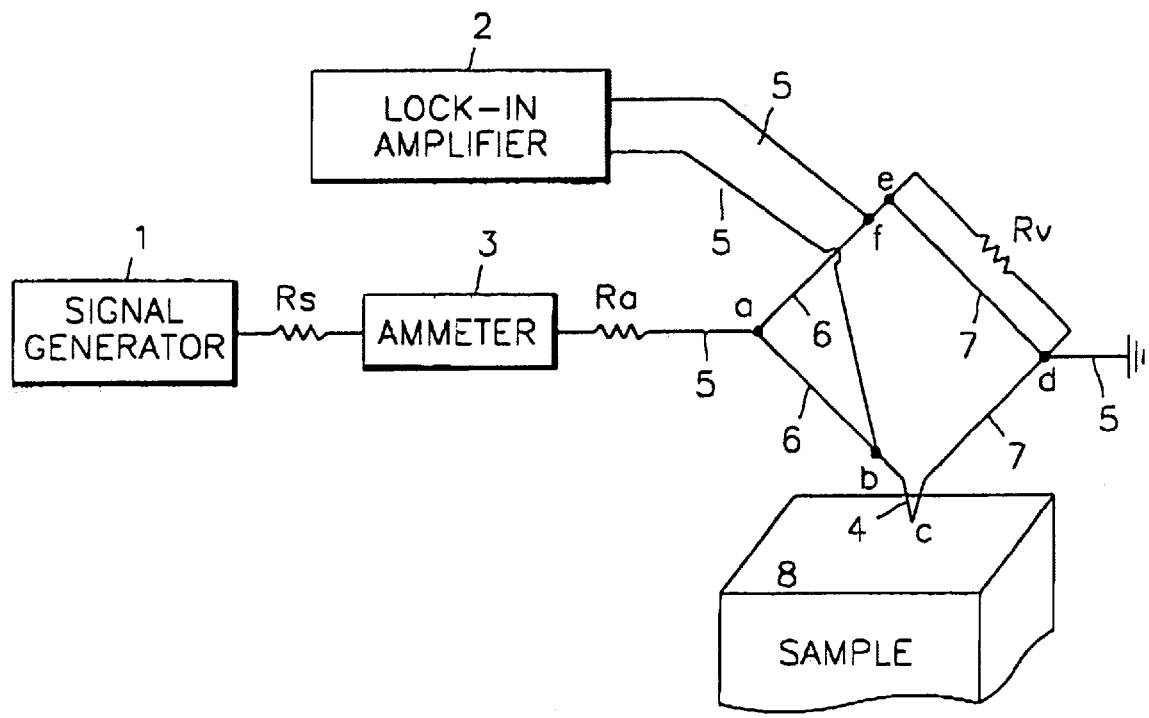
FIG. 1 shows the configuration of an apparatus for measuring thermal properties and making thermomechanical modifications on a material surface with a Peltier tip according to the present invention.

Referring to FIG. 1, an apparatus for measuring thermal properties of and making thermomechanical modifications on a material surface using a Peltier tip according to the present invention includes a signal generator 1, a lock-in amplifier 2, an ammeter 3, and a bridge circuit. The bridge circuit includes metallic wires 6 and 7 made of different metals, a Peltier tip 4, and a variable resistor Rv.

More specifically, the signal generator 1 with output resistance s is connected to one terminal of the ammeter 3 with internal resistance Ra. The other terminal of the ammeter 3 is connected to the central point of the metallic wire 6. The metallic wires 6 and 7 are joined to form the bridge circuit. One junction point in the bridge circuit is the Peltier tip 4. The central point of the metallic wire 7 is grounded. To eliminate an Ohmic voltage drop, the variable resistor Rv is added to the bridge circuit.

The lock-in amplifier 2 is connected to a point b of the Peltier tip 4 and a point f, and the Peltier tip 4 contacts the surface of a material 8 of which thermal properties are to be measured.

The locations of points in the bridge circuit, which connect the lock-in amplifier 2, will now be described. In general, in a measurement of AC voltage between the ends of a resistor when current flows, the signals of second and third harmonics as well as a fundamental frequency signal are generated by Joule heating. The second and third harmonic signals have small amplitudes that are proportional to a temperature coefficient of the resistor. When a signal to be measured is of very small amplitude, the measurement may be affected by these higher harmonic signals. Also, as frequency increases, the amplitude of harmonic signals produced by reactance of a circuit component increases in proportion with the frequency. Thus, connecting the symmetrical points of the bridge circuit to the lock-in amplifier 2 is effective in eliminating these unnecessary harmonic signals.

Figure 2:
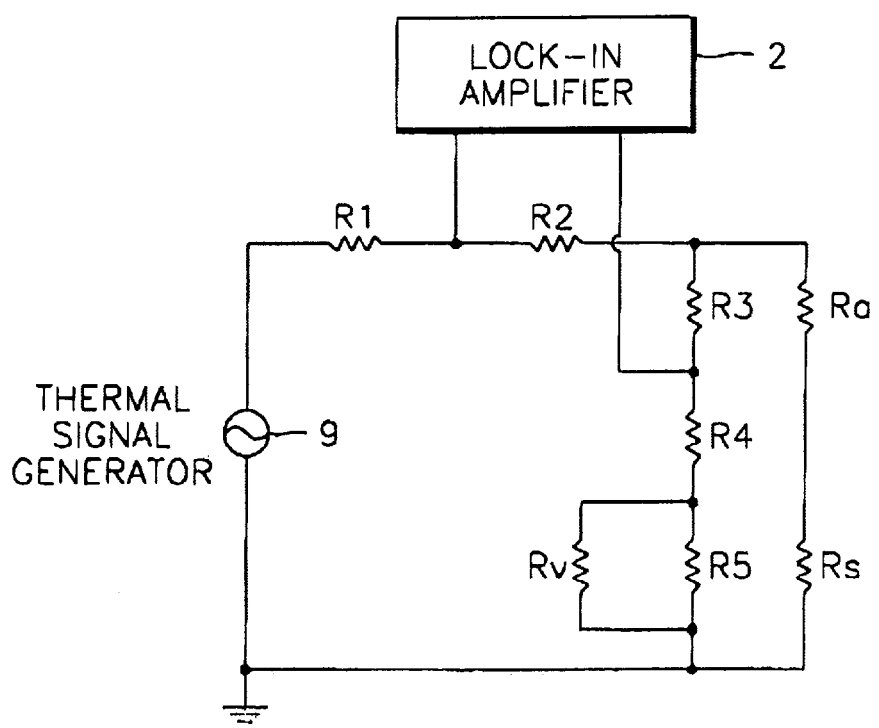
FIG. 2 is an equivalent circuit of the apparatus of FIG. 1 for measuring thermal properties of a material surface, wherein the Peltier tip can be replaced with a thermal signal generator.

FIG. 2 is an equivalent circuit of the circuit of FIG. 1 for measuring thermal properties of the material 8. In the equivalent circuit of FIG. 2, the Peltier tip 4 can be replaced with a thermal signal generator 9 since thermal oscillation is converted into voltage oscillation by Seebeck effect.

If a junction point e is thermally grounded, the lock-in amplifier 2 obtains thermal properties of the surface of the material B by measuring the voltage between junction points b and f in a complex plane. Here, R1 denotes resistance of the metallic wire 6 between the junction points b and c of FIG. 1 and R2 denotes resistance of the metallic wire 6 between the junction points a and b. R3 denotes resistance of the metallic wire 6 between the junction points a and f, and R4 denotes resistance of the metallic wire 6 between the junction points e and f. R5 denotes resistance of the metallic wire 7 between the junction points d and e, and R6 denotes resistance of the metallic wire 7 between the junction points c and d. Ra, Rs, and Rv denote the internal resistance of the ammeter 3, the output resistance of the signal generator 1, and the variable resistance, respectively The Peltier effect will now be described. The Peltier effect refers to a phenomenon in which, when current is applied to a junction of different metallic wires 7 and 8 at a temperature T, the time derivative of heat Q or power is generated at the junction due to the electrochemical potential difference between the two conductors, as expressed by Equation (1):

$$\frac{dQ}{dt} = T\Delta SI \qquad (1)$$

where ΔS denotes the difference in a thermoelectric power between the two conductors and I denotes current.

Thus, the junction point may be heated or cooled depending on the direction of current I. From the tabulated value ΔS for a pair of various metallic wires (thermocouple) at an arbitrary temperature, and the current I, a precise estimation of power given to a material can be made, Thermocouples consisting of the metallic wires 6 and 7 having different characteristics includes include a J-type thermocouple, which is an iron (Fe)—constantan (Cu—Ni) junction, a K-type thermocouple, which is a chromel (Ni—Cr)—alumel (Ni—Al), a T-type thermocouple, which is a copper (Cu)—constantan (Cu—Ni) junction, an E-type thermocouple, which is a chrornel (Ni—Cr)—constantan (Cu—Ni) junction, an N-type thermocouple, which is a nicosil (Ni—Cr—Si)—nisil (Ni—Si—Mg) junction, R- and S-type thermocouples, which are platinum (Pt)—platinum (Pt) and rhodium (Rh) alloy junctions, and G-C- and D-type thermocouples, which are a tungsten (W)—tungsten (W) and rhenium (Re) alloy junction. The choice of a thermocouple depends on temperature range and its sensitivity.

When the signal generator 1 drives a current at specific frequency, the current is input to the bridge circuit through the ammeter 3. The current passes through routes a-e-d and a-b-c-d to a ground. The junctions are constructed such that junction points a, b, and f are junctions of the copper wire 5 and the metallic wire 6, junction points c and e are junctions of the two metallic wires 6 and 7, and junction point d is a junction of the metallic wire 7 and the copper wire 5. Temperature oscillations occur at each junction point due to thermal exchange caused by Peltier effect. The amplitudes of these temperature oscillations varies depending on various conditions such as specific heat of a junction material, thermal conductivity, geometry of thermal diffusion, oscillation frequency, and mass of a junction. Here, junction points a, b, d, and f are junctions of the copper wire 5 and the metallic wire 6, and the junction points a, b, d, and f are thermally grounded with metals such as gold, silver, and copper to eliminate temperature oscillations at those junctions.

The junction point e can be treated in two ways. A first method is that junction point e is thermally grounded like in junction points a, b, d, and f. In this case, temperature oscillation caused by heat exchange occur only at junction point c. The temperature oscillation results in voltage oscillation due to the Seebeck effect at that junction point. The lock-in amplifier 2 reads the difference in voltage between the junction points b and f in a complex plane. As shown in FIG. 1, the voltage measured by the lock-in amplifier 2 is induced by the Ohmic voltage drop, as well as by the temperature oscillation in the Peltier tip 4. The Ohmic voltage drop can be removed by the variable resistor Rv using a well-known Wheatstone bridge correction approach. Thus, only the voltage induced by temperature oscillation can be measured.

A second method is that the junction point e is made in the form of a tip like junction point c. In this case, if the material 8 does not contact the tip junction pant c, no signal is detected due to symmetry of the bridge circuit. On the other hand, if the material 8 contacts junction point c, only the difference between temperature oscillations at the tip e itself and temperature oscillation on the material surface is measured.

If current is applied to the Peltier tip 4, heat exchange occurs only at the junction. Thus, the Peltier tip 4 in contact with the material surface works as a point heat source and as a point temperature sensor simultaneously. Due to the facts, measurement of thermal properties on a material surface can be done with high spatial resolution and sensitivity. Furthermore, since a thermal diffusion length is proportional to one over square root of a driving frequency, it is possible to control and enhance the spatial resolution. When thermal properties of the material 8 are measured using the Peltier tip 4, driving frequency can be increased to several kHz, and the thermal wavelength becomes several tens of micrometers for a material with high thermal conductivity and several hundreds of nanometers for a material with low thermal conductivity. That is, it is possible to measure thermal properties at higher spatial resolution.

According to the present invention, thermal properties are measured and thermal modifications are made on a material surface by using the Peltier tip 4 which works as a heat source and as a temperature sensor simultaneously. The fact that heat exchange occurs only at a junction offers a way to thermally characterize a material surface with submicron-scale spatial resolution and sensitivity and high sensitivity while providing high spatial resolution and speed for thermal modifications since heating and cooling simultaneously at a Peltier tip.

What is claimed is:

1. An apparatus for measuring thermal and thermomechanical properties of a surface of a material using a Peltier tip, the apparatus comprising:

a Peltier tip;

a signal generator that supplies an electric current to a Peltier tip;

an ammeter connected to the signal generator for measuring the current, a bridge circuit including junctions of metallic wires, connected to the ammeter, wherein one junction of metallic wires is the Peltier tip; and a lock-in amplifier connected to symmetrical terminals of the bridge circuit for amplifying and detecting voltage due to temperature oscillation detected by the Peltier tip.

2. The apparatus of claim 1, wherein the bridge circuit includes a correction resistor connected in parallel with terminals of the bridge circuit in order to remove an Ohmic voltage caused by the signal generator.

3. The apparatus of claim 1, wherein the bridge circuit includes junctions of different metallic wires, in order to measure a difference between temperature oscillations when the Peltier tip contacts the material and when the Peltier tip does not contact the material.

4. The apparatus of claim 1, wherein the bridge circuit includes functions which are thermally grounded with a metal.

* * * * *